United States Patent
Binmoeller et al.

(10) Patent No.: US 8,454,632 B2
(45) Date of Patent: Jun. 4, 2013

(54) TISSUE ANCHOR FOR SECURING TISSUE LAYERS

(75) Inventors: Kenneth F. Binmoeller, Rancho Santa Fe, CA (US); Fiona M. Sander, Los Altos Hills, CA (US); Michael P. Allen, Los Altos, CA (US); Matthew Yurek, San Diego, CA (US)

(73) Assignee: Xlumena, Inc., Mountain View, CA (US)

( * ) Notice: Subject to any disclaimer, the term of this patent is extended or adjusted under 35 U.S.C. 154(b) by 20 days.

(21) Appl. No.: 12/427,215

(22) Filed: Apr. 21, 2009

(65) Prior Publication Data
US 2009/0281557 A1 Nov. 12, 2009

Related U.S. Application Data

(60) Provisional application No. 61/052,460, filed on May 12, 2008.

(51) Int. Cl.
*A61B 17/08* (2006.01)

(52) U.S. Cl.
USPC .......................................................... 606/151

(58) Field of Classification Search
USPC ................. 606/139, 151, 153–158, 213, 215, 606/216
See application file for complete search history.

(56) References Cited

U.S. PATENT DOCUMENTS

| | | | |
|---|---|---|---|
| 2,127,903 A * | 8/1938 | Bowen | ........................... 606/154 |
| 3,039,468 A | 6/1962 | Price | |
| 3,717,151 A | 2/1973 | Collett | |
| 3,874,388 A | 4/1975 | King et al. | |
| 3,970,090 A | 7/1976 | Loiacono | |
| 4,235,238 A | 11/1980 | Ogiu et al. | |
| 4,608,965 A | 9/1986 | Anspach, Jr. et al. | |
| 4,705,040 A | 11/1987 | Mueller et al. | |
| 4,790,813 A | 12/1988 | Kensey | |
| 4,896,678 A | 1/1990 | Ogawa | |
| 4,950,285 A | 8/1990 | Wilk | |
| 4,973,317 A | 11/1990 | Bobrove | |
| 4,990,139 A | 2/1991 | Jang | |
| 5,024,655 A | 6/1991 | Freeman et al. | |
| 5,064,435 A | 11/1991 | Porter | |
| 5,180,392 A | 1/1993 | Skeie et al. | |

(Continued)

FOREIGN PATENT DOCUMENTS

| | | |
|---|---|---|
| DE | 102006050385 | 4/2008 |
| EP | 637431 A1 | 2/1995 |

(Continued)

OTHER PUBLICATIONS

Chopita et al., "Endoscopic Gastroenteric Anastomosis Using Magnets," Endoscopy. 2005 Apr;37(4):313-317.

(Continued)

*Primary Examiner* — Thomas McEvoy
(74) *Attorney, Agent, or Firm* — Shay Glenn LLP

(57) ABSTRACT

Tissue anchors comprise a woven filament braid body having an elongated tubular configuration and a foreshortened configuration where proximal and distal ends of the body expand radially into double-walled flange structures while leaving a cylindrical saddle region therebetween. The tissue anchors are deployed through penetrations between adjacent tissue layers, where the flanges engage the outer surfaces of the tissue layers and the saddle region resides within the tissue penetrations.

6 Claims, 9 Drawing Sheets

U.S. PATENT DOCUMENTS

| | | | |
|---|---|---|---|
| 5,183,464 A | 2/1993 | Dubrul | |
| 5,197,971 A | 3/1993 | Bonutti | |
| 5,207,229 A | 5/1993 | Winters | |
| 5,209,727 A | 5/1993 | Radisch, Jr. et al. | |
| 5,211,651 A | 5/1993 | Reger et al. | |
| 5,224,945 A | 7/1993 | Pannek, Jr. | |
| 5,234,447 A | 8/1993 | Kaster et al. | |
| 5,258,000 A | 11/1993 | Gianturco | |
| 5,261,920 A | 11/1993 | Main et al. | |
| 5,275,610 A | 1/1994 | Eberbach | |
| 5,275,611 A | 1/1994 | Behl | |
| 5,290,249 A | 3/1994 | Foster et al. | |
| 5,304,198 A | 4/1994 | Samson | |
| 5,330,497 A | 7/1994 | Freitas et al. | |
| 5,353,785 A | 10/1994 | Wilk | |
| 5,372,588 A | 12/1994 | Farley et al. | |
| 5,395,349 A | 3/1995 | Quiachon et al. | |
| 5,443,484 A | 8/1995 | Kirsch et al. | |
| 5,458,131 A | 10/1995 | Wilk | |
| 5,462,561 A | 10/1995 | Voda | |
| 5,470,337 A | 11/1995 | Moss | |
| 5,495,851 A | 3/1996 | Dill et al. | |
| 5,520,700 A | 5/1996 | Beyar et al. | |
| 5,536,248 A | 7/1996 | Weaver et al. | |
| 5,620,456 A | 4/1997 | Sauer et al. | |
| 5,620,457 A | 4/1997 | Pinchasik et al. | |
| 5,662,664 A | 9/1997 | Gordon et al. | |
| 5,688,247 A | 11/1997 | Haindl et al. | |
| 5,697,944 A | 12/1997 | Lary | |
| 5,709,671 A | 1/1998 | Stephens et al. | |
| 5,709,707 A | 1/1998 | Lock et al. | |
| 5,713,870 A | 2/1998 | Yoon | |
| 5,716,325 A | 2/1998 | Bonutti | |
| 5,725,552 A | 3/1998 | Kotula et al. | |
| 5,797,906 A | 8/1998 | Rhum et al. | |
| 5,817,062 A | 10/1998 | Flom et al. | |
| 5,827,276 A | 10/1998 | LeVeen et al. | |
| 5,843,116 A | 12/1998 | Crocker et al. | |
| 5,843,127 A | 12/1998 | Li | |
| 5,853,421 A | 12/1998 | Leschinsky et al. | |
| 5,855,576 A | 1/1999 | LeVeen et al. | |
| 5,857,999 A | 1/1999 | Quick et al. | |
| 5,858,006 A | 1/1999 | Van der Aa et al. | |
| 5,882,340 A | 3/1999 | Yoon | |
| 5,893,856 A | 4/1999 | Jacob et al. | |
| 5,897,567 A | 4/1999 | Ressemann et al. | |
| 5,935,107 A | 8/1999 | Taylor et al. | |
| 5,944,738 A | 8/1999 | Amplatz et al. | |
| 5,951,576 A | 9/1999 | Wakabayashi | |
| 5,951,588 A | 9/1999 | Moenning | |
| 5,957,363 A | 9/1999 | Heck | |
| 5,993,447 A | 11/1999 | Blewett et al. | |
| 6,007,522 A | 12/1999 | Agro et al. | |
| 6,007,544 A | 12/1999 | Kim | |
| 6,017,352 A | 1/2000 | Nash et al. | |
| 6,022,359 A | 2/2000 | Frantzen | |
| 6,036,698 A | 3/2000 | Fawzi et al. | |
| 6,080,174 A | 6/2000 | Dubrul et al. | |
| 6,113,609 A | 9/2000 | Adams | |
| 6,113,611 A | 9/2000 | Allen et al. | |
| 6,190,353 B1 | 2/2001 | Makower et al. | |
| 6,228,039 B1 | 5/2001 | Binmoeller | |
| 6,231,587 B1 | 5/2001 | Makower | |
| 6,241,758 B1 | 6/2001 | Cox | |
| 6,251,084 B1 | 6/2001 | Coelho | |
| 6,290,485 B1 | 9/2001 | Wang | |
| 6,309,415 B1 | 10/2001 | Pulnev et al. | |
| 6,334,446 B1 | 1/2002 | Beyar | |
| 6,348,064 B1 | 2/2002 | Kanner | |
| 6,358,264 B2 | 3/2002 | Banko | |
| 6,371,964 B1 | 4/2002 | Vargas et al. | |
| 6,371,965 B2 | 4/2002 | Gifford et al. | |
| 6,391,036 B1 | 5/2002 | Berg et al. | |
| 6,402,770 B1 | 6/2002 | Jessen | |
| 6,436,119 B1 | 8/2002 | Erb et al. | |
| 6,447,524 B1 | 9/2002 | Knodel et al. | |
| 6,447,533 B1 | 9/2002 | Adams | |
| 6,451,042 B1 | 9/2002 | Bonutti | |
| 6,454,765 B1 | 9/2002 | LeVeen et al. | |
| 6,475,185 B1 | 11/2002 | Rauker et al. | |
| 6,475,222 B1 | 11/2002 | Berg et al. | |
| 6,485,496 B1 | 11/2002 | Suyker et al. | |
| 6,488,653 B1 | 12/2002 | Lombardo | |
| 6,508,252 B1 | 1/2003 | Berg et al. | |
| 6,520,908 B1 | 2/2003 | Ikeda et al. | |
| 6,535,764 B2 | 3/2003 | Imran et al. | |
| 6,575,967 B1 | 6/2003 | LeVeen et al. | |
| 6,610,100 B2 | 8/2003 | Phelps et al. | |
| 6,614,595 B2 | 9/2003 | Igarashi | |
| 6,616,675 B1 | 9/2003 | Evard et al. | |
| 6,620,122 B2 | 9/2003 | Stinson et al. | |
| 6,626,919 B1 | 9/2003 | Swanstrom | |
| 6,632,197 B2 | 10/2003 | Lyon | |
| 6,635,068 B1 | 10/2003 | Dubrul et al. | |
| 6,638,213 B2 | 10/2003 | Ogura et al. | |
| 6,645,205 B2 | 11/2003 | Ginn | |
| 6,655,386 B1 | 12/2003 | Makower et al. | |
| 6,656,206 B2 | 12/2003 | Corcoran et al. | |
| 6,669,708 B1 | 12/2003 | Nissenbaum et al. | |
| 6,682,536 B2 | 1/2004 | Vardi et al. | |
| 6,736,828 B1 | 5/2004 | Adams et al. | |
| 6,746,472 B2 | 6/2004 | Frazier et al. | |
| 6,746,489 B2 * | 6/2004 | Dua et al. | 623/23.68 |
| 6,749,621 B2 | 6/2004 | Pantages et al. | |
| 6,773,440 B2 | 8/2004 | Gannoe et al. | |
| 6,835,189 B2 | 12/2004 | Musbach et al. | |
| 6,902,535 B2 | 6/2005 | Eberhart et al. | |
| 6,916,332 B2 | 7/2005 | Adams | |
| 6,921,361 B2 | 7/2005 | Suzuki | |
| 6,921,387 B2 | 7/2005 | Camrud | |
| 6,942,678 B2 | 9/2005 | Bonnette et al. | |
| 6,960,233 B1 | 11/2005 | Berg et al. | |
| 6,966,917 B1 | 11/2005 | Suyker et al. | |
| 6,974,467 B1 | 12/2005 | Gonzales, Jr. | |
| 7,018,401 B1 | 3/2006 | Hyodoh et al. | |
| 7,056,325 B1 | 6/2006 | Makower et al. | |
| 7,074,229 B2 | 7/2006 | Adams | |
| 7,077,850 B2 | 7/2006 | Kortenbach | |
| 7,125,413 B2 | 10/2006 | Grigoryant | |
| 7,150,723 B2 | 12/2006 | Meguro et al. | |
| 7,153,314 B2 | 12/2006 | Laufer | |
| 7,156,857 B2 | 1/2007 | Pasrich | |
| 7,169,161 B2 | 1/2007 | Bonnette et al. | |
| 7,182,771 B1 | 2/2007 | Houser et al. | |
| 7,204,842 B2 | 4/2007 | Geitz | |
| 7,273,451 B2 | 9/2007 | Sekine et al. | |
| 7,303,531 B2 | 12/2007 | Lee et al. | |
| 7,309,341 B2 | 12/2007 | Ortiz et al. | |
| 7,361,180 B2 | 4/2008 | Saadat et al. | |
| 7,377,897 B1 | 5/2008 | Kunkel et al. | |
| 7,416,554 B2 | 8/2008 | Lam et al. | |
| 7,429,264 B2 | 9/2008 | Melkent et al. | |
| 7,534,247 B2 | 5/2009 | Ortiz | |
| 7,591,828 B2 | 9/2009 | Ortiz | |
| 7,845,536 B2 | 12/2010 | Viola et al. | |
| 7,942,890 B2 | 5/2011 | D'Agostino et al. | |
| 7,998,155 B2 | 8/2011 | Manzo | |
| 8,034,063 B2 | 10/2011 | Binmoeller | |
| 8,187,289 B2 | 5/2012 | Tacchino et al. | |
| 2001/0011170 A1 | 8/2001 | Davison et al. | |
| 2002/0183787 A1 | 12/2002 | Wahr et al. | |
| 2002/0188301 A1 | 12/2002 | Dallara et al. | |
| 2003/0014063 A1 | 1/2003 | Houser et al. | |
| 2003/0032975 A1 | 2/2003 | Bonutti | |
| 2003/0040803 A1 | 2/2003 | Rioux et al. | |
| 2003/0045893 A1 | 3/2003 | Ginn | |
| 2003/0050665 A1 | 3/2003 | Ginn | |
| 2003/0069533 A1 | 4/2003 | Kakutani et al. | |
| 2003/0073979 A1 | 4/2003 | Naimark et al. | |
| 2003/0078604 A1 | 4/2003 | Walshe | |
| 2003/0088256 A1 | 5/2003 | Conston et al. | |
| 2003/0093118 A1 | 5/2003 | Ho et al. | |
| 2003/0109900 A1 | 6/2003 | Martinek | |
| 2003/0120292 A1 | 6/2003 | Park et al. | |
| 2003/0163017 A1 | 8/2003 | Tam et al. | |
| 2004/0019322 A1 | 1/2004 | Hoffmann | |
| 2004/0034371 A1 | 2/2004 | Lehman et al. | |

| | | |
|---|---|---|
| 2004/0049157 A1 | 3/2004 | Plishka et al. |
| 2004/0073108 A1 | 4/2004 | Saeed et al. |
| 2004/0236346 A1 | 11/2004 | Parker |
| 2004/0243122 A1 | 12/2004 | Auth et al. |
| 2004/0249985 A1 | 12/2004 | Mori et al. |
| 2004/0260332 A1 | 12/2004 | Dubrul et al. |
| 2005/0033327 A1 | 2/2005 | Gainor et al. |
| 2005/0043781 A1 | 2/2005 | Foley |
| 2005/0059990 A1 | 3/2005 | Ayala et al. |
| 2005/0075654 A1 | 4/2005 | Kelleher |
| 2005/0096685 A1 | 5/2005 | Murphy et al. |
| 2005/0113868 A1 | 5/2005 | Devellian et al. |
| 2005/0187567 A1 | 8/2005 | Baker et al. |
| 2005/0228413 A1 | 10/2005 | Binmoeller et al. |
| 2005/0251159 A1 | 11/2005 | Ewers et al. |
| 2005/0251208 A1 | 11/2005 | Elmer et al. |
| 2005/0277981 A1* | 12/2005 | Maahs et al. .................. 606/213 |
| 2006/0062996 A1 | 3/2006 | Chien et al. |
| 2006/0111672 A1 | 5/2006 | Seward |
| 2006/0116697 A1 | 6/2006 | Carter et al. |
| 2006/0142703 A1 | 6/2006 | Carter et al. |
| 2006/0142790 A1 | 6/2006 | Gertner |
| 2006/0167482 A1 | 7/2006 | Swain et al. |
| 2006/0190021 A1 | 8/2006 | Hausman et al. |
| 2006/0200177 A1 | 9/2006 | Manzo |
| 2006/0217748 A1* | 9/2006 | Ortiz ............................. 606/153 |
| 2006/0217762 A1 | 9/2006 | Maahs et al. |
| 2006/0224183 A1 | 10/2006 | Freudenthal |
| 2006/0259051 A1 | 11/2006 | Nissl |
| 2006/0259074 A1 | 11/2006 | Kelleher et al. |
| 2006/0282087 A1 | 12/2006 | Binmoeller |
| 2007/0027534 A1 | 2/2007 | Bergheim et al. |
| 2007/0066863 A1 | 3/2007 | Rafiee et al. |
| 2007/0112363 A1 | 5/2007 | Adams |
| 2007/0123840 A1 | 5/2007 | Cox |
| 2007/0123917 A1 | 5/2007 | Ortiz et al. |
| 2007/0123934 A1 | 5/2007 | Whisenant et al. |
| 2007/0135825 A1 | 6/2007 | Binmoeller |
| 2007/0179426 A1 | 8/2007 | Selden |
| 2007/0197862 A1 | 8/2007 | Deviere et al. |
| 2007/0213812 A1 | 9/2007 | Webler et al. |
| 2007/0260273 A1 | 11/2007 | Cropper et al. |
| 2008/0009888 A1 | 1/2008 | Ewers et al. |
| 2008/0045989 A1 | 2/2008 | Welborn |
| 2008/0065012 A1 | 3/2008 | Hebert et al. |
| 2008/0071301 A1 | 3/2008 | Matsuura et al. |
| 2008/0077180 A1 | 3/2008 | Kladakis et al. |
| 2008/0243151 A1 | 10/2008 | Binmoeller et al. |
| 2008/0249481 A1 | 10/2008 | Crainich et al. |
| 2009/0024149 A1 | 1/2009 | Saeed et al. |
| 2009/0030380 A1 | 1/2009 | Binmoeller |
| 2009/0082803 A1 | 3/2009 | Adams et al. |
| 2009/0143713 A1 | 6/2009 | Van Dam et al. |
| 2009/0143759 A1 | 6/2009 | Van Dam et al. |
| 2009/0143760 A1 | 6/2009 | Van Dam et al. |
| 2009/0177288 A1 | 7/2009 | Wallsten |
| 2010/0130993 A1 | 5/2010 | Paz et al. |
| 2010/0261962 A1 | 10/2010 | Friedberg |
| 2010/0268029 A1 | 10/2010 | Phan et al. |
| 2010/0268175 A1 | 10/2010 | Lunsford et al. |
| 2011/0071350 A1 | 3/2011 | Van Dam et al. |
| 2011/0112622 A1 | 5/2011 | Phan et al. |
| 2011/0137394 A1 | 6/2011 | Lunsford et al. |
| 2012/0109277 A1 | 5/2012 | Lepulu et al. |

FOREIGN PATENT DOCUMENTS

| | | |
|---|---|---|
| EP | 1314404 | 5/2003 |
| EP | 1314404 A3 | 9/2003 |
| EP | 1520526 A1 | 4/2005 |
| EP | 1520532 A2 | 4/2005 |
| JP | S58-35219 | 3/1983 |
| JP | H05-329165 | 12/1993 |
| JP | H05-508563 | 12/1993 |
| JP | H07-096038 | 4/1995 |
| JP | 2001-511658 | 8/2001 |
| JP | 2001-275947 | 10/2001 |
| JP | 2002-119516 | 4/2002 |
| JP | 2003-526448 | 9/2003 |
| JP | 2004-512153 | 4/2004 |
| JP | 2004-216192 | 8/2004 |
| JP | 2005-525865 | 9/2005 |
| JP | 2007514462 | 6/2007 |
| WO | WO 97/27898 | 8/1997 |
| WO | WO 01/21247 A1 | 3/2001 |
| WO | WO 01/72367 A1 | 10/2001 |
| WO | WO 03/020106 A2 | 3/2003 |
| WO | WO 03/071962 A2 | 9/2003 |
| WO | WO 2005/011463 A2 | 2/2005 |
| WO | WO 2005/096953 A1 | 10/2005 |
| WO | 2006/062996 | 6/2006 |
| WO | WO 2006/115811 A1 | 11/2006 |
| WO | WO 2006/062996 A3 | 4/2009 |
| WO | WO 2010/011445 A1 | 1/2010 |

OTHER PUBLICATIONS

International Search Report and Written Opinion of PCT Application No. PCT/US2009/043445, mailed Jul. 1, 2009, 9 pages total.

International Search Report and Written Opinion of PCT Application No. PCT/US2009/043496, mailed Jul. 17, 2009, 8 pages total.

Kahaleh et al., "Interventional EUS-guided cholangiography: evaluation of a technique in evolution" (2006) Gastrointestinal Endoscopy 64(1):52-59.

Kwan et al., "EUS-guided cholecystenterostomy: a new technique," (2007) Gastrointestinal Endoscopy 66(3):582-586.

U.S. Appl. No. 12/427,254, filed Apr. 21, 2009; first named inventor: Kenneth F. Binmoeller.

Phan et al.; U.S. Appl. No. 13/364,265 entitled "Apparatus and Method for Deploying Stent Across Adjacent Tissue Layers," filed Feb. 1, 2012.

Lepulu et al.; U.S. Appl. No. 13/363,297 entitled "Apparatus and Method for Penetrating and Enlarging Adjacent Tissue Layers," filed Jan. 31, 2012.

Fritscher-Ravens et al.; A through-the-scope device for suturing and tissue approximation under EUS control; Gastro Endo; 56(5); pp. 737-742; Nov. 2002.

Fritscher-Ravens et al.; Transgastric gastropexy and hiatal hernia repair for GERD under EUS control: A porcine model; Gastro Endo; 59(1); pp. 89-95; Jan. 2004.

Swain et al.; Knot tying at flexible endoscopy; gastro endo; 40(6); pp. 722-729; Nov. 1994.

* cited by examiner

TISSUE ANCHOR FOR SECURING TISSUE LAYERS

CROSS-REFERENCES TO RELATED APPLICATIONS

This application claims the benefit of provisional application 61/052,460, filed on May 12, 2008, the full disclosure of which is incorporated herein by reference. The disclosure of this application is related to those of Ser. No. 12/427,254, filed on the same day as the present application.

BACKGROUND OF THE INVENTION

1. Field of the Invention

The present invention relates generally to medical methods and devices. In particular, the present invention relates to tissue anchors and methods for their use in fastening adjacent tissue layers in medical procedures.

Tissue approximation is useful in many medical procedures for a variety of purposes. In the broadest definition, tissue apposition may be performed by a number of conventional procedures, such as suturing, gluing, energy-mediated fusion, and the like. Of particular interest to the present invention, however, is the use of tissue fasteners which are positioned through penetrations in adjacent tissue layers and deployed to physically hold or anchor the tissue layers together.

A number of tissue-anchoring systems have been devised over the years. Many prior art tissue anchors include expandable cage structures, often referred to as malecotts, or "molybolts," at opposite ends of a shaft, where the cages are expanded and deployed on each side of the layered tissues to be anchored together. One exemplary tissue anchor employing expandable structural elements on each side of a shaft for anchoring the esophagus to the stomach wall is described in commonly-owned, copending U.S. patent publication no. 2005/0228413. In some instances, the mechanical tissue fasteners may provide or define a central lumen or passage, typically to allow for drainage from one body lumen or cavity into another. Such fasteners are often referred to as "stents," with an exemplary stent for draining a pseudocyst described in U.S. Pat. No. 6,620,122. The '122 stent has a barbell-like configuration with open cuffs at each end. The cuffs are not reinforced and do not provide significant strength for holding adjacent tissue structures together, particularly when the tissue structures tend to separate as the patient moves about.

While usable for many purposes, the tissue anchors of the prior art have often been either too rigid, providing good attachment but presenting substantial risk of tissue necrosis or adhesion, or too weak, presenting little risk of tissue damage but allowing leakage and movement at the point of tissue penetration.

Thus, for these reasons, it would be beneficial to provide alternative or improved tissue anchors and methods for their deployment and use, where the anchors can provide firm attachment of tissue while minimizing the risk of necrosis and other damage to the tissue. The tissue anchors should preferably be suitable for attachment both with and without a central lumen for fistula formation. The tissue anchors should be deliverable endoscopically to a wide variety of body lumens for a wide variety of purposes. Additionally, it would be desirable if the tissue anchors were removable, both during initial implantation procedures as well as in a subsequent procedure(s) many weeks, months, or even years following the initial implantation. At least some of these objectives will be met by the inventions described hereinbelow.

2. Description of the Background Art

US 2003/069533 describes an endoscopic transduodenal biliary drainage system which is introduced through a penetration, made by a trans-orally advanced catheter having a needle which is advanced from the duodenum into the gall bladder. U.S. Pat. No. 6,620,122 describes a system for placing a self-expanding stent from the stomach into a pseudocyst using a needle and an endoscope. US 2005/0228413, commonly assigned with the present application, describes a tissue-penetrating device for endoscopy or endosonography-guided (ultrasonic) procedures where an anchor may be placed to form an anastomosis between body lumens, including the intestine, stomach, and gallbladder. See also U.S. Pat. No. 5,458,131; U.S. Pat. No. 5,495,851; U.S. Pat. No. 5,944,738; U.S. Pat. No. 6,007,522; U.S. Pat. No. 6,231,587; U.S. Pat. No. 6,655,386; U.S. Pat. No. 7,273,451; U.S. Pat. No. 7,309,341; US 2004/0243122; US 2004/0249985; US 2007/0123917; WO 2006/062996; EP 1314404 Kahaleh et al. (2006) *Gastrointestinal Endoscopy* 64:52-59; and Kwan et al. (2007) *Gastrointestinal Endoscopy* 66:582-586.

BRIEF SUMMARY OF THE INVENTION

Tissue anchors according to the present invention comprise a body formed from a woven filament braid. The filament will typically be a metal wire, more typically being a nickel-titanium or other super-elastic or shape memory metal wire. Alternatively, in cases where elasticity is less critical, a filament could be formed from a polymeric material, such as polypropylene, polyethylene, polyester, nylon, PTFE, or the like. In some cases, a bioabsorbable or bio-degradable material, typically a biodegradable polymer, such as poly-L-lactic acid (PLLA), could find use.

The body will have both an elongated tubular configuration and a foreshortened configuration where proximal and distal ends of the body expand radially (as the body is foreshortened) into double-walled flange structures. Such "double-walled flange structures" are formed as a portion of the body, typically an end-most portion but optionally some portion spaced inwardly from the end, moves inwardly (toward the middle) so that a pair of adjacent body segments within the portion are drawn together at their bases so that a midline or a crest line bends and expands radially to form a pair of adjacent annular rings which define the double-walled flange structure. After such foreshortening and deployment of the double-walled flange structures, the body will further have a cylindrical saddle region between the flange structures. When the anchor is deployed in tissue, the flange structures engage the outer surfaces of adjacent tissue layers and the saddle region typically resides within a penetration through the tissue layers.

When formed from shaped memory metal wires, such as nitinol or eligiloy, the wires will have a relatively small diameter, typically in the range from 0.001 inch to 0.02 inch, usually from 0.002 inch to 0.01 inch, where the braid will include from as few as 10 to as many as 200 wires, more commonly being from 20 wires to 100 wires. In exemplary cases, the wires will be round having diameters in the range from 0.003 into the 0.007 inch with a total of from 24 to 60 wires. The wires are braided into a tubular geometry by conventional techniques, and the tubular geometry will be heat-treated to impart the desired shape memory. Usually, the braided tube will be formed into the desired final (deployed) configuration with the flanges at each end. Such a flanged configuration will then be heat set or formed into the braid so that, in the absence of a radially constraining or axially elongating force, the anchor will assume the foreshortened configuration with the flanges at each end. Such foreshortened-memory configurations will allow the anchor to be delivered in a constrained configuration (either radially or axially elongated) and thereafter released from constraint so that the body assumes the flanged configuration at the target site.

In alternative embodiments, however, the woven filament braid will be heat set into the elongated tubular configuration and shifted into the foreshortened, flanged configuration by applying an axial compressive force. Such axial compression will foreshorten and radially expand the flanges. The flanges may be preferentially formed by providing sleeves, tubes, rods, filaments, tethers, or the like, which apply force to the tube to create the flanges while leaving the cylindrical saddle region unexpanded or expanded to a lesser degree. Optionally, the body may have weakened regions, reinforced regions, or be otherwise modified so that the desired flange geometries are formed when a force is applied to cause axial foreshortening.

The tissue anchors will be adapted to be delivered by a delivery device, typically an endoscopic delivery catheter, usually having a small diameter in the range from 1 mm to 8 mm, usually from 2 mm to 5 mm. Thus, the elongated tubular configuration of the anchor body will usually have a diameter less than that of the catheter diameter, usually from 0.8 mm to 7.5 mm, more usually from 0.8 mm to 4.5 mm, where the double-walled flanged structures will be expandable significantly, usually being in the range from 3 mm to 70 mm, more usually in the range from 5 mm to 40 mm. The cylindrical saddle region of the anchor will often not increase in diameter during deployment, but may optionally increase to a diameter from 2 mm to 50 mm, more usually from 5 mm to 20 mm. When present, the lumen or passage through the deployed tissue anchor can have a variety of diameters, typically from as small as 0.2 mm to as large as 40 mm, more usually being in the range from 1 mm to 20 mm, and typically having a diameter which is slightly smaller than the expanded diameter of the cylindrical saddle region. The length of the body may also vary significantly. Typically, when in the elongated tubular configuration, the body will have a length in the range from 7 mm to 100 mm, usually from 12 mm to 70 mm. When deployed, the body will be foreshortened, typically by at least 20%, more typically by at least 40% and often by 70% or greater. Thus, the foreshortened length will typically be in the range from 2 mm to 80 mm, usually in the range from 2.5 mm to 60 mm, and more usually being in the range from 3 mm to 40 mm.

The body of the tissue anchor may consist of the woven filament braid with no other coverings or layers. In other instances, however, the tissue anchor may further comprise a membrane or other covering formed over at least a portion of the body. Often, the membrane is intended to prevent or inhibit tissue ingrowth to allow the device to be removed after having been implanted for weeks, months, or longer. Suitable membrane materials include polytetrafluoroethylene (PTFE), expanded PTFE (ePTFE), silicone, polypropylene, urethane polyether block amides (PEBA), polyethyleneterephthalate (PET), polyethylene, C-Flex® thermoplastic elastomer, Krator® SEBS and SBS polymers, and the like.

Such membranes may be formed over the entire portion of the anchor body or only a portion thereof, may be formed over the exterior or interior of the body, and will typically be elastomeric so that the membrane conforms to the body in both the elongated and foreshortened configurations. Optionally, the membrane may be formed over only the central saddle region, in which case it would not have to be elastomeric when the central saddle region does not radially expand.

The strength of the double-walled flanged structures will depend on the number, size, stiffness, and weave pattern(s) of the individual wires used to form the tubular anchor body. For example, a design with a large number of nitinol wires, for example 48, but a relatively small wire diameter, for example 0.006 inches, will form a braid structure with a saddle region which remains flexible and double-walled flanges which are relatively firm. Use of fewer wires, for example 16, and a larger wire diameter, for example 0.016 inches, will form a braid structure with a relatively rigid saddle region and relatively stiff, non-flexible flanges. Usually, the more flexible design is desirable. In particular, it is preferred that the double-walled flange structures have a preselected bending stiffness in the range from 1 g/mm to 100 g/mm, preferably in the range from 4 g/mm to 40 g/mm. Similarly, it is preferred that the central saddle region have a preselected bending stiffness in the range from 1 g/mm to 100 g/mm, preferably from 10 g/mm to 100 g/mm.

The bending stiffness of the flange can be determined by the following test. The distal flange is secured in a fixture. The outer diameter of the flange is pulled in a direction parallel to the axis of the tissue anchor using a hook attached to a Chatillon force gage. The saddle of anchor is held in a hole in a fixture and force (grams) and deflection (mm) are measured and recorded. The bending stiffness of the flange can be determined by the following test. The distal flange is secured in a fixture. The outer diameter of the flange is pulled in a direction perpendicular to axis of the tissue anchor using a hook attached to a Chatillon force gage. The saddle of anchor is held in a hole in a fixture and force (grams) and deflection (mm) are measured and recorded.

While it will usually be preferred to form the self-expanding anchor bodies from shape memory alloys, other designs could employ elastic tethers which join the ends of the body together. Thus, the bodies could have a low elasticity, where the force for axially compressing the ends comes from the elastic tethers. Such designs may be particularly suitable when polymeric or other less elastic materials are being used for the body of the anchor.

In still other embodiments, the tissue anchors may comprise a lock which maintains the body in a foreshortened configuration. For example, the lock may comprise a rod or a cylinder within the body which latches to both ends of the body when the body is foreshortened. Alternatively, the lock could comprise one, two, or more axial members which clamp over the lumen of the anchor body when the body is foreshortened.

As a still further option, the tissue anchor could comprise a sleeve formed over a portion of the cylindrical saddle region. The sleeve will both maintain the diameter of the central saddle region and will limit the inward extension of the flanges, help forming the flanges as the anchor body is axially foreshortened.

In still other embodiments, the body of the tissue anchor will be expanded by applying an axial compression to the ends of the body (i.e., drawing the ends toward each other, not by self-expansion). Usually, the body in such embodiments will be pre-shaped or pre-formed to assume its elongated tubular configuration when not subjected to axial compression. Only by applying an axially compressive force will the flanges be formed at the ends. The force may be applied in a variety of ways. Most commonly, at least one axial member will be attached to one end of the body, where the axial member can be pulled to foreshorten the body. The axial member may comprise a plurality of tethers. In a particular example, the tethers will lie over the exterior of the body in the saddle region lying within a lumen of the body within the flange regions. Alternatively, the axial member may comprise a rod or cylinder which is disposed within the lumen of the body. In particular, the cylinder may be attached at one end of the body and pulled toward the other end to deploy the flanges. When the body is fully deployed, the cylinder may be attached to the other end of the body, thus providing an open lumen through the body. In those embodiments where the flanges are deployed by applying an axial compression to the body, it will usually be necessary to provide a lock to hold the body in the foreshortened configuration. A variety of specific lock structures are described hereinbelow.

In another aspect of the present invention, systems for delivering the tissue anchor are provided. The self-expanding tissue anchors may be delivered using a delivery catheter comprising a sheath which covers the tissue anchor body, or a mandrel which extends through a central lumen of the anchor body, to hold the body in its elongated tubular configuration. By then retracting the sheath or advancing the tissue anchor relative to the sheath, the body of the anchor is released from constraint and the flanges are allowed to radially expand. For use with the tissue anchors which require the application of an axial force for deployment, the delivery catheter will comprise an actuator which releasably holds the tissue anchor and which includes a mechanism for engaging and pulling (axially tensioning) the axial member to expand the flanges and deploy the anchor.

In still other aspects of the present invention, methods for approximating tissue comprising forming aligned penetrations in two or more adjacent tissue layers. The tissue anchor is then advanced through the penetrations, where the tissue anchor comprises a body formed from the woven filament braid. The body is in an elongated tubular configuration while being advanced and is subsequently foreshortened to cause a distal end and a proximal end of the body to each deform into double-walled flange structures on opposite sides of the adjacent tissue layers. A cylindrical saddle region remains on the anchor body between the deployed flanges, where the flanges are able to press against the tissue layers to provide the approximating force. Typically, the body will be foreshortened to a degree selected to apply sufficient pressure to the tissues to hold them together without causing significant tissue injury or necrosis. Usually, the applied pressure will be in the range from 0.005 g/mm$^2$ to 5 g/mm$^2$, usually from 0.2 g/mm$^2$ to 1 g/mm$^2$.

The methods of the present invention are useful for holding a wide variety of adjacent tissue layers together, where the tissues are typically selected from the group consisting of the esophagus, stomach, duodenum, small intestine, large intestine, bile duct, pancreatic duct, gallbladder, pancreas, pancreatic pseudocyst, liver, diaphragm, and crus muscle and adjoining tissues. The anchor is typically formed and advanced by positioning a catheter near a target location on the tissue wall within a body lumen. The penetrating element is then advanced from the catheter to form the penetrations, and the catheter is advanced through the penetrations to position the tissue anchor therethrough prior to foreshortening. Foreshortening may comprise either of the approaches described above. That is, foreshortening may comprise releasing the elongated tubular body from constraint so that the flanges self-expand. Alternatively, the foreshortening may comprise applying an axial tension to the anchor body to draw the ends closer, thus deploying the flanges radially outwardly.

DETAILED DESCRIPTION OF THE INVENTION

Figure 1:
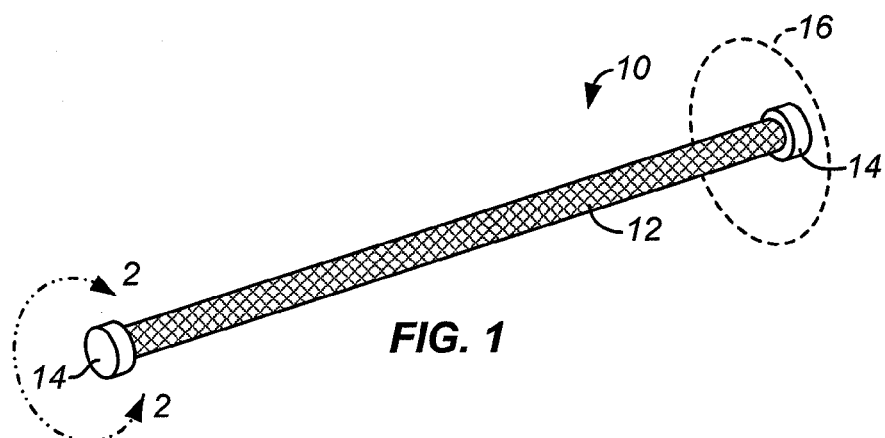
FIG. 1 illustrates a first exemplary tissue anchor constructed in accordance with the principles of the present invention.

As shown in FIG. 1, tissue anchor 10 constructed in accordance with the principles of the present invention comprises a body 12 having caps 14 at each end thereof. The body 12 comprises a woven filament braid, as discussed in more detail above, and is illustrated in its elongated tubular configuration. In this particular embodiment, the body 12 will be formed from a super elastic material, typically nitinol or eligiloy, and will be heat set, so that in the absence of radial constraint or an axially elongating force, the body will revert to its memory configuration having double-walled flanges formed at each end. One of the flanges 16 is shown in broken line in FIG. 1, while FIGS. 3A-3F illustrate various configurations of the flanges 16.

Figure 1A:
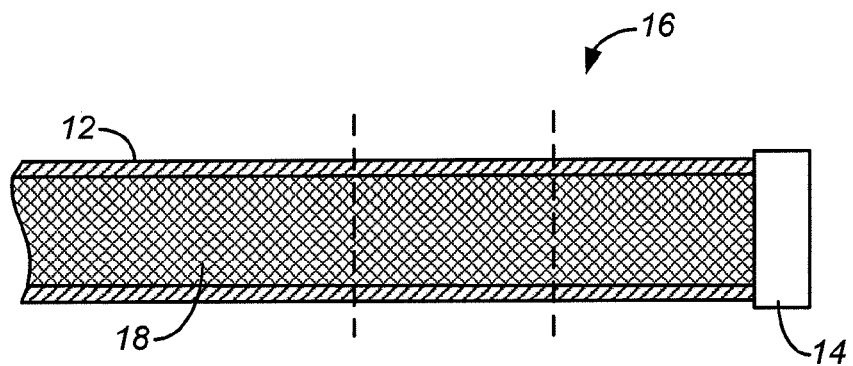
FIGS. 1A-1C illustrate formation of a double-walled anchor structure in an end of the tissue anchor.
Figure 1B:
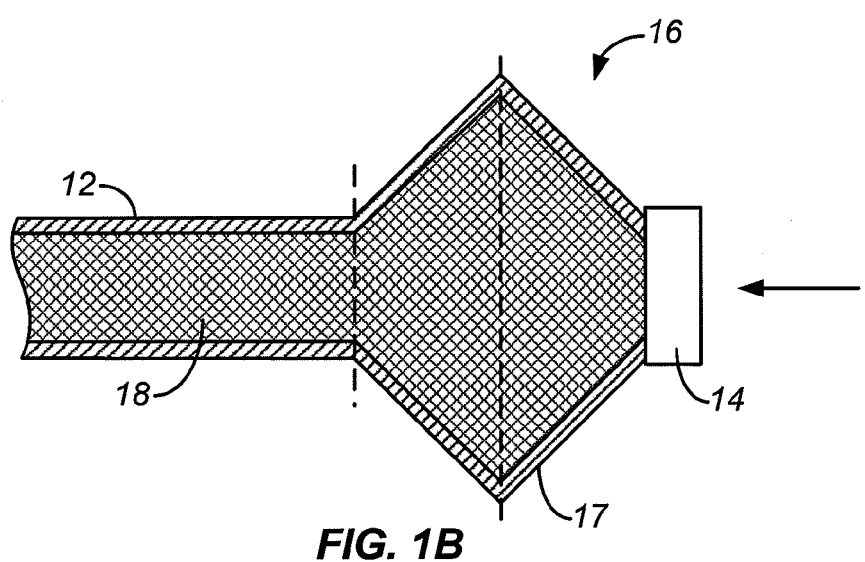
Figure 1C:
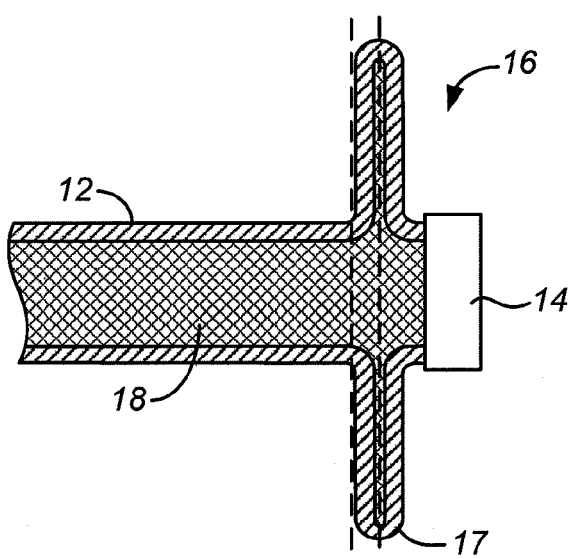

Referring now to FIGS. 1A-1C, the double-walled flange structure 16 forms as the end of tubular body 12 axially foreshortens. Initially, the end of the tubular body 12 is maintained in its tubular configuration, as shown in FIG. 1A. Maintenance of the tubular configuration can be achieved in various ways, such as using an external tubular sheath or other restraint (not shown), by using a mandrel or other elongate structure which is advanced through an inside lumen or passage 18 of the body to engage the end and/or occupy the entire lumen in order to maintain the tubular configuration, or the like. Once the constraint is removed, the pre-formed or memory shape of the double-walled flange structure will begin to form, as shown in FIG. 1B. The end of the tubular structure 12 will move toward the middle of the tubular structure, as shown by the arrow in FIG. 1B, and a preformed ridge 17 will appear, eventually collapsing into the double-walled flange structure 16 as illustrated in FIG. 1C. While the above description is directed at embodiments where the tubular body 12 has been preformed to have the double-walled flange structure 16 as part of its memory, the general change in geometry will also be true for those anchors where an axially compressive force must be applied in order to deploy the flanges. In such cases, the tubular body may have preformed scoring or other weakened regions which preferentially allow the woven braid to bend in the manner illustrated in FIGS. 1A-1C.

Figure 2A:
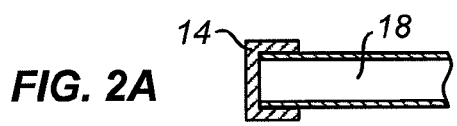
FIGS. 2A-2C illustrate alternate distal end constructions of the tissue anchor of FIG. 1, taken along line 2-2 thereof.
Figure 2B:
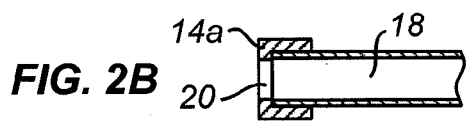
Figure 2C:

The end caps 14 will be provided when it is desired to constrain the end of the anchor body 12 to prevent the end(s) from expanding. In some instances, the end cap 14 will have a solid face, as shown in FIG. 2A, which will close the inside lumen or passage 18 to prevent or inhibit the flow of body fluids therethrough. Alternatively, the end cap 14a may be formed with a passage 20 therethrough to allow for its flow through lumen 18 (FIG. 2B). In a still further alternate embodiment, as shown in FIG. 2C, the tissue anchor 10 may not include any end caps, allowing the end to expand in certain embodiments.

Figure 3A:
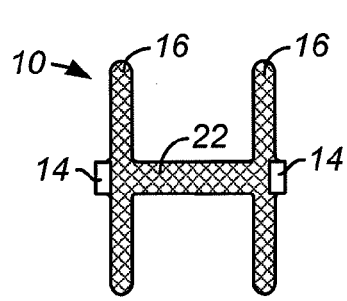
FIGS. 3A-3F illustrate alternative deployments and modifications to the exemplary tissue anchor of FIG. 1.
Figure 3B:
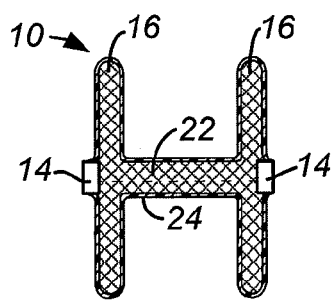
Figure 3C:
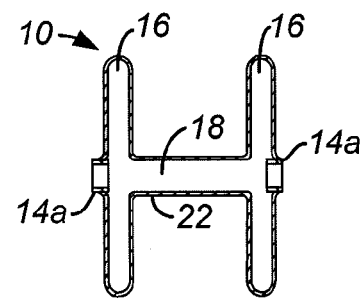
Figure 3D:
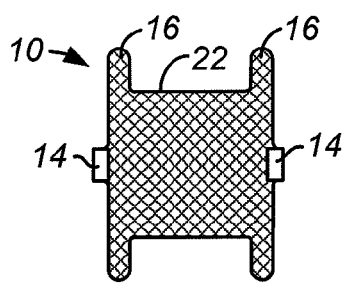
Figure 3E:
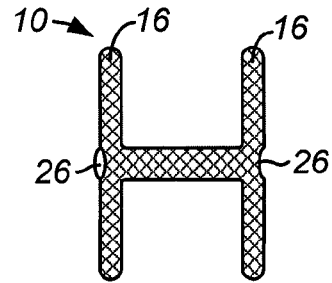
Figure 3F:
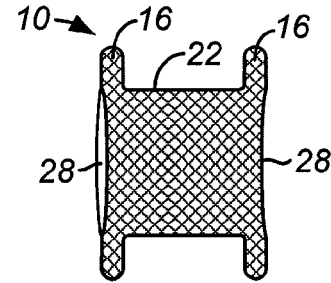

Referring now to FIGS. 3A through 3F, various deployment configurations for the tissue anchor 10 will be described (where the tissue anchor 10 is assumed to have the same elongated starting length in each illustrated deployment). In FIG. 3A, the flanges 16 expand radially while a central saddle region 22 does not expand. In FIG. 3B, the central saddle region 22 does not significantly expand but has a somewhat greater deployed length than that of the embodiment of FIG. 3A, resulting in flanges 16 having a slightly smaller diameters. FIG. 3B also illustrates a covering or membrane 24 over the entire exterior of the tissue anchor 10, thus inhibiting tissue ingrowth and/or minimizing fluid leakage when the anchor is implanted. In FIG. 3C, tissue anchor 10 includes the open end caps 14a providing an open lumen 18 therethrough. In FIG. 3D, a tissue anchor 10 having a central saddle region 22 with a significantly expanded diameter is illustrated. In FIG. 3E, the tissue anchor 10 having open ends 26 (that is, they are free from the end cap as illustrated in FIG. C) is illustrated. Passages 26 are shown to have generally the same diameter as the tubular body 22 in its non-deployed configuration. In contrast, in FIG. 3F, open ends 28 are shown having diameters which are significantly greater than the non-deployed diameter of the anchor body. Similarly, the central saddle region 22 of FIG. 3F is also significantly greater than the diameter of the non-deployed tissue anchor. It will be appreciated that the tissue anchors of the present invention may have a wide variety of configurations with different lengths, saddle region diameters, flange diameters, open lumens, closed lumens, membrane-covered surfaces, partially membrane-covered surfaces, and the like.

Figure 4A:
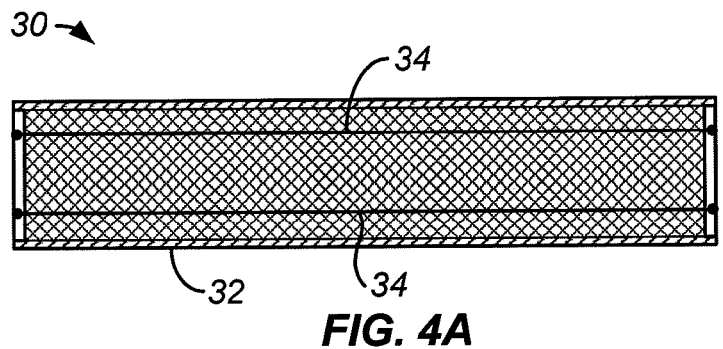
FIGS. 4A and 4B illustrate the tissue anchor employing elastic tethers for deployment.
Figure 4B:
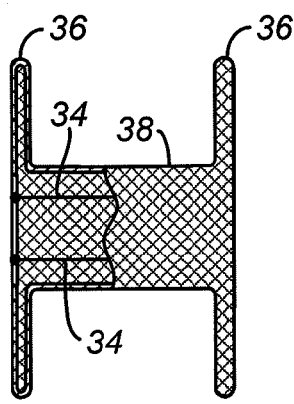

Referring now to FIGS. 4A and 4B, a tissue anchor 30 having an alternative construction is illustrated. The body 32 of tissue anchor 30 is not pre-shaped, forming the enlarged flanges as a result of axial shortening. For example, elastic tethers 34 are provided which apply the axially compressive force to foreshorten the ends and form double-walled flanges 36, as illustrated in FIG. 4B. The resulting shape may be controlled by providing reinforcement over a central saddle region 38 to prevent that region from axially foreshortening and/or radially expanding. Alternatively, the central saddle region 38 could be fused together to prevent deformation. In the device of FIGS. 4A and 4B, the tissue anchor can be deployed through a tissue tract while the exterior is radially constrained or the or the ends axially lengthened. When released from the radial constraint, or axial tension, the elastic tethers will foreshorten the ends, forming double walled flanges where the saddle size (flange diameter, saddle length, saddle diameter) will conform exactly to the anatomy. Thus, the geometry will be "self-adjusting". Reinforcement over the central saddle region is not necessary but could be utilized if desired for other purposes.

Figure 5A:
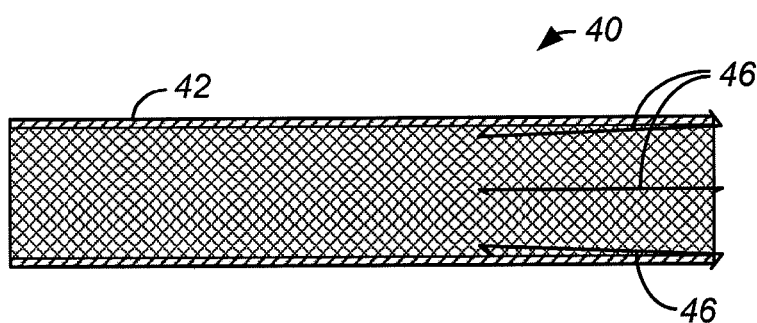
FIGS. 5A and 5B illustrate a tissue anchor having latching elements.
Figure 5B:
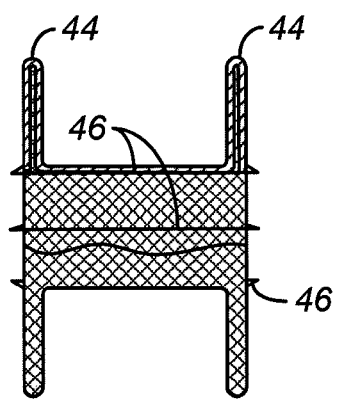

Referring now to FIGS. 5A and 5B, a tissue anchor 40 comprises a tubular body 42 which has both an elongated tubular configuration (as shown in FIG. 5A) and an axially foreshortened configuration with double-walled flanges 44, as shown in FIG. 5B. The tubular body 44 could either be of the self-expanding type or, alternatively, could require an axial compressive force to foreshorten the body into the configuration of FIG. 5B. In either case, the tissue anchor 40 will be provided with a locking structure including a plurality of axial bars 46 which lock over the ends of the deployed tissue anchor 40, as illustrated in FIG. 5B.

Figure 6A:
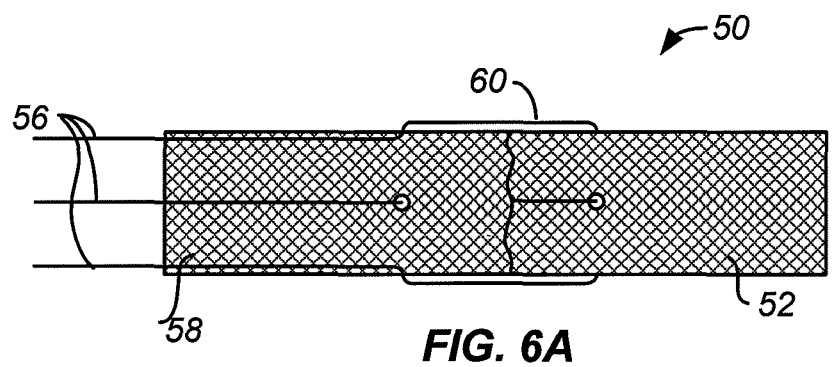
FIGS. 6A and 6B illustrate a tissue anchor having tethers for applying an axial force for foreshortening and deployment.
Figure 6B:
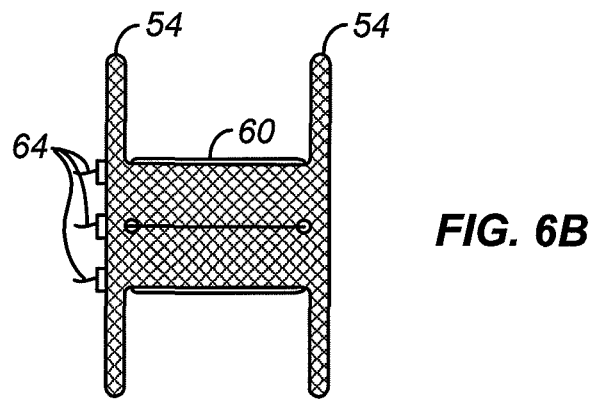

Referring now to FIGS. 6A and 6B, a tissue anchor 50 comprises an anchor body 52 which requires an axially compressive force in order to foreshorten the body to form the double-walled flanges 54, as shown in FIG. 6B. The axially compressive force is provided by a plurality of tethers 56 which extend through a lumen or central passage 58 of the body 52 through the flange region and which then extend outwardly over the central saddle region 60 before passing back into the interior of the body. By then pulling on the tethers 56 relative to the body 52, the flange regions will be axially compressed to radially expand, as shown in FIG. 6B, while and the central saddle region 60 may radially expand to an extent which depends on the braid configuration, the size and compliance of the lumen through which the device passes, and the force applied to the tethers. After the flanges have been deployed, the tethers may be locked in place, typically by a locking device 64, such as crimping pledgets, use of a unidirectional slide or other ratcheting lock device, or use of a slip-knot or a sliding element that relies on friction to secure its position.

Figure 7A:
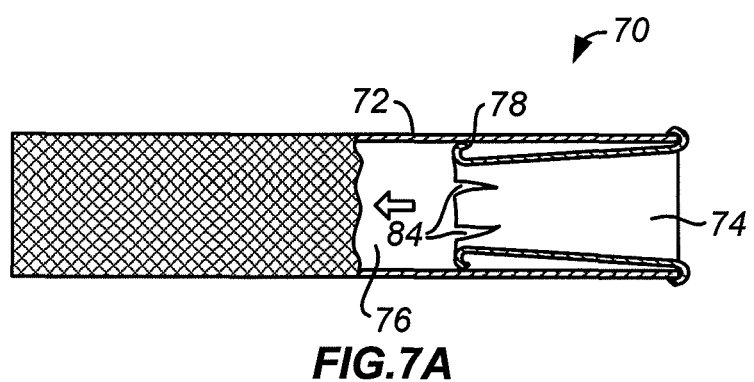
FIGS. 7A and 7B illustrate a tissue anchor having an internal cylinder for applying an axially compressive force and latching the anchor in its deployed configuration.
Figure 7B:
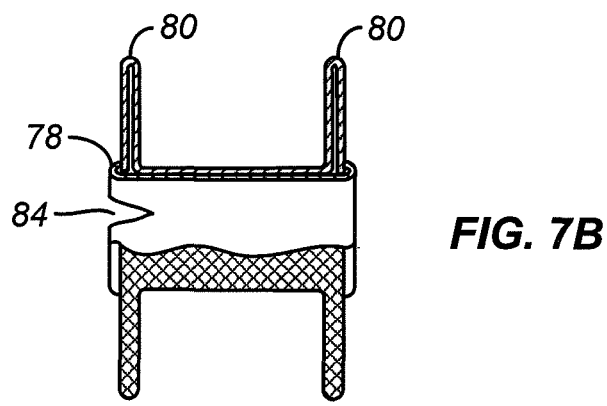

A tissue anchor 70, as illustrated in FIGS. 7A and 7B, comprises an anchor body 72 having a locking cylinder 74 in one end of the lumen or central passage 76. The anchor body 72 may be axially foreshortened by drawing on the free end of the locking cylinder 74 and pulling the cylinder in the direction of the arrow until a locking end 78 of the cylinder engages the far end of the deployed flange 80. Not only does the cylinder 74 act as an element to foreshorten the anchor body 72, it also acts as the lock to hold the anchor body open and provides a smooth cylindrical surface for the lumen to permit fluid flow or provide other access. Conveniently, the locking end 78 of the cylinder 74 may be provided with notches or other apertures to allow that end to be collapsed within the lumen 76 and to snap back open as it is pulled past the flange 80 to which it will lock.

Figure 8A:
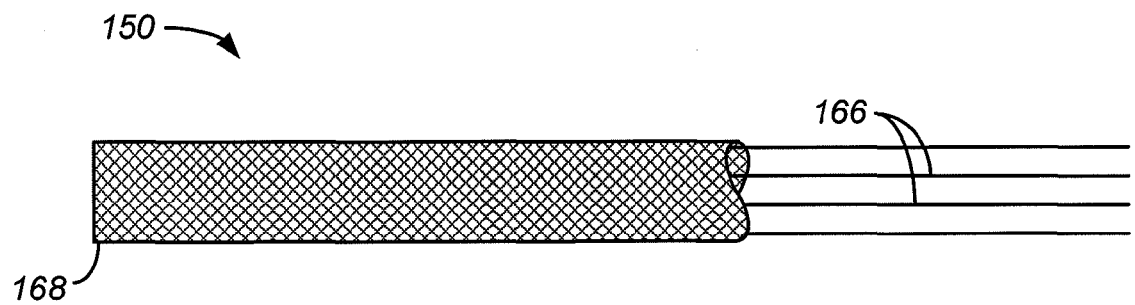
FIGS. 8A and 8B illustrate another stent design having tethers to effect foreshortening and radial expansion.
Figure 8B:
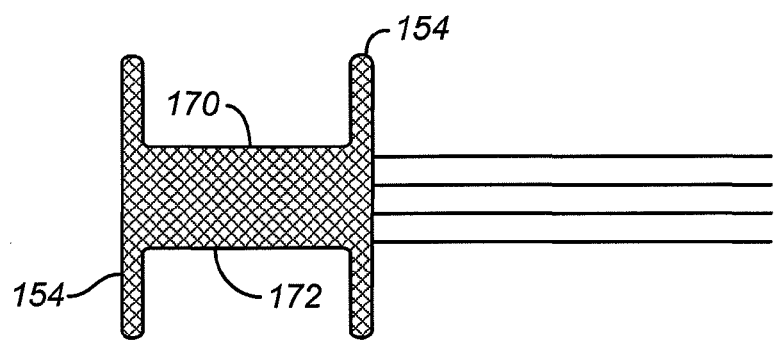

Referring now to FIGS. 8A and 8B, an exemplary tissue anchor or stent 150 comprises a counterwound, braided stent body, typically formed from a polymer such as polypropylene, polyester, nylon, or PEEK; a metal, such stainless steel, nitinol, or eligiloy; a bioabsorbable material, such as polyglycolic acid, lactic acid, caprolactone, polydioxanone, cat or bovine intestine; a natural fiber, such as silk or cotton; or mixtures, composites, or co-constructions of any of the above. Tethers 166 are provided which are connected at the remote end 168 of the stent, and which, when drawn in the direction away from the duodenum or other originating body lumen, will foreshorten the stent to create the flanges 154, as described previously. Drawing the tethers 166 in the proximal direction opens and maintains the central lumen 172 of deployed stent 150 to provide the luminal conduit which allows flow between anatomical lumens, such as the gallbladder, GB and intestine. A reduced diameter central region 170 is located between the flanges 154. The width of the central region 170 may be controlled optionally by placing a restraining element, such as a cylinder or struts 172 over the stent to prevent radial expansion. Thus, the stent 150 will automatically adjust to the thickness of the luminal walls. A restraint is not needed since the tissue geometry, particularly the tract dilation either before or after anchor placement, will provide a barrier which will restrain expansion of the central region and determine the length of the saddle region.

In another embodiment (not illustrated), the stent 150 can have proximal and distal ends connected centrally by an extensible material allowing the deployed stent to facilitate apposition of opposing luminal walls and minimize pressure necrosis.

Figure 9:
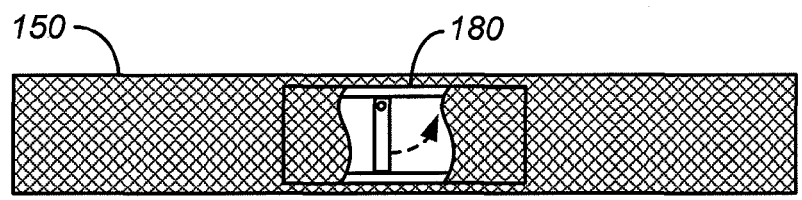
FIG. 9 illustrates a stent having a one-way flow valve according to the present invention.

Referring now to FIG. 9, in some instances it will be desirable to provide a one-way flow element 180, such as a flat valve, within the interior of the stent 150. By properly orienting the stent, the one-way flow control element can then allow drainage from the gallbladder into the intestines while substantially inhibiting or blocking reflux flow back from the stomach into the gallbladder. Additionally, the flow control element 180 could serve as a restraint to define the central region 170 of the stent when expanded. Alternative valve designs include a sock valve placed within the interior or at the proximal end of the foreshortened anchor, a "duck bill" valve, a flapper valve, a spring-loaded ball valve, or other spring-loaded element, such as a tapered pin or plug.

Figure 10:
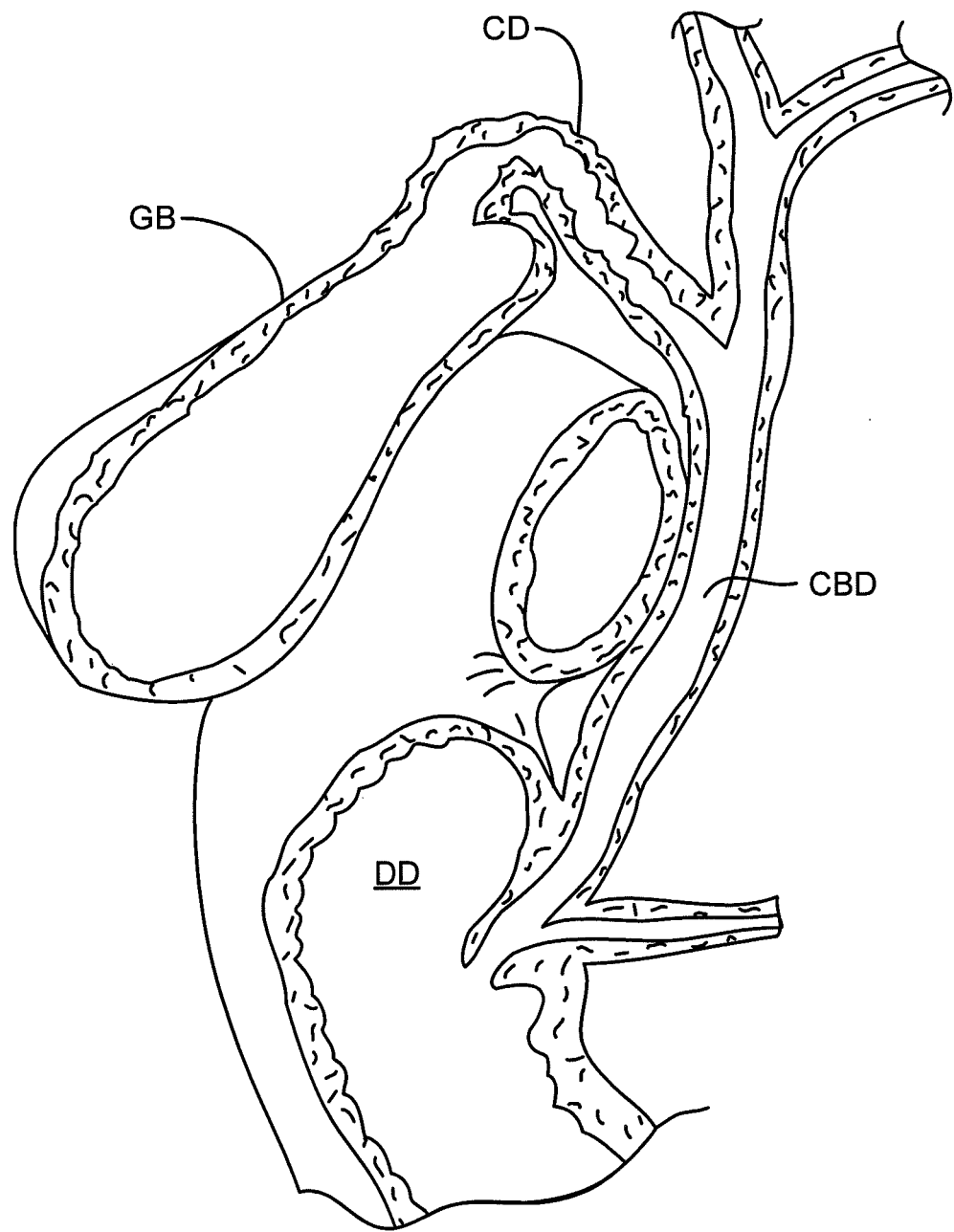
FIG. 10 illustrates a patient's anatomy including cross sections of the gallbladder and duodenum.

Use of the tissue anchors of the present invention for draining a gallbladder will now be described. The biliary system of a patient (FIG. 10) includes the gallbladder GB which is connected to the cystic duct CD which feeds into the common bile duct CBD. The common bile duct, in turn, feeds bile into the descending part of the duodenum DD. While the present invention will be described with particular reference to attachment between the gallbladder GB and the descending duodenum DD, the principles apply to connecting a variety of other luminal structures, including the esophagus, the crus, the fundus, the bile duct, the intestines, and the like.

Figure 11:
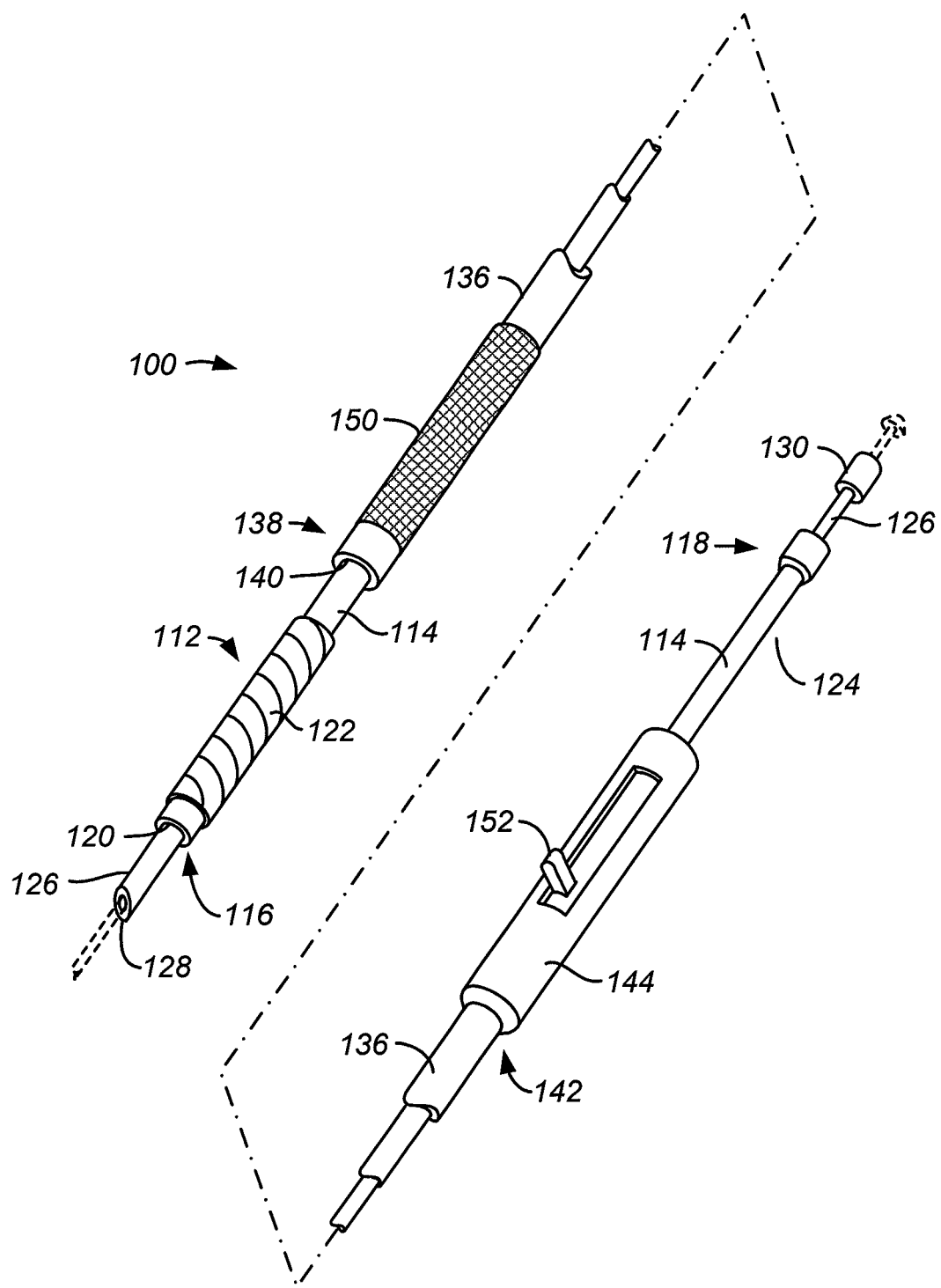
FIG. 11 illustrates an exemplary system for penetrating the intestinal and gallbladder walls in accordance with the principles of the present invention.

Referring now to FIG. 11, a system for connecting luminal walls and placing a stent to establish a flow path therebetween is illustrated. This system 100 is particularly useful for connecting a wall of the gallbladder to an intestinal wall, such as the duodenal wall or a stomach wall, but it will be appreciated that the system can find other uses in establishing other anastomotic connections, such as between the biliary duct including but not limited to the common bile duct, cystic duct and/or the pancreatic duct and the stomach, intestine or any part of the gastrointestinal tract. System 100 can also be used to create a connection to any fluid collection including but not limited to a pancreatic pseudocyst, abdominal fluid collections including ascites, pleural effusions and abscesses in any accessible location or the like. System 100 is also useful to create a connection between the urinary bladder and any part of the gastrointestinal tract.

The luminal wall connection system of the present invention comprises a catheter 112 including a catheter body 114 having a distal end 116 and a proximal end 118. The catheter body 114 has a lumen extending therethrough, with a distal port 120 of the lumen being visible in FIG. 11. An inflatable balloon 122 is mounted on the distal end of the catheter body 114 and an inflation lumen (not shown) is provided in the wall of the catheter body and connected to an inflation port 124 near the proximal end of the catheter body 114.

A needle 126 having a sharpened distal tip 128 is received within the lumen of the catheter body 114 and is slidably received so that it can be selectively advanced from and/or retracted into the distal port 120, as illustrated in FIG. 11. A handle or grip 130 is provided at the proximal end of the needle 126 to facilitate manipulation.

An outer tubular member 136 is coaxially received over the catheter body 114 and includes a distal end 138 having a distal port 140 through which the catheter body 114 projects. Proximal end 142 of the outer tubular body 136 is connected to handle 144. Catheter body 114 extends through the handle, allowing the catheter of balloon 122 to be selectively extended and retracted relative to both the outer tube 136 and needle 126.

The expandable tissue anchor/stent 150 is carried near the distal end 138 of the outer tubular body 136. The stent is optionally expanded in a variety of ways, including balloon expansion, self-expansion (where the stent would be released from constraint), heat-induced expansion of heat-sensitive alloy, such as nitinol, or the like. In the presently preferred embodiment, the stent 150 will comprise a polymer braid which may be foreshortened to induce radial expansion. This particular design was described in more detail above with reference to FIGS. 8A and 8B. The handle 144 will include a thumb slide 152 for effecting expansion of the stent 150 typically by pulling on tethers attached to the stent, as described below. A variety of other expansion mechanisms could be employed, for example, by pushing on the proximal end of the stents with rods or other pushing elements while a distal portion of the stent remains constrained.

Figure 12A:
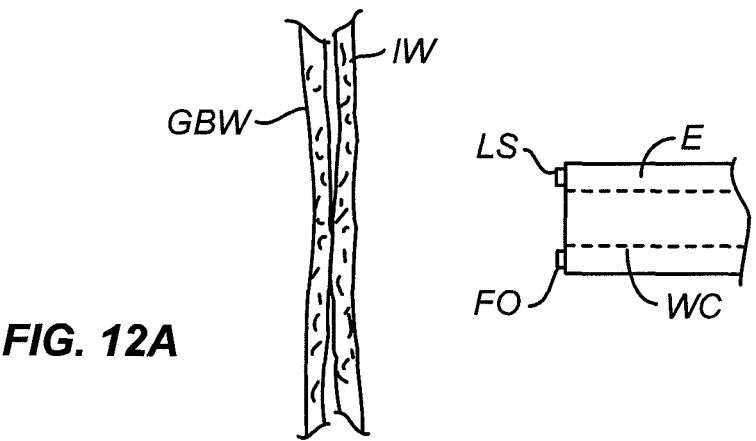
FIGS. 12A-12G illustrate the method of the present invention for establishing a flow path between the gallbladder and the intestines in accordance with the principles of the present invention.

Referring now to FIGS. 12A-12E, deployment of the stent 150 to attach gallbladder wall GBW to an intestinal wall IW will be described. Initially, an endoscope E will usually be transorally introduced so that it is within the intestines and can image the gallbladder to locate a target site for the anastomotic connection, as illustrated in FIG. 12A. The endoscope will usually include at least a light source LS and a fiber optic image cable, or in some instances a CCD or other miniature camera, or ultrasound transducer. The endoscope will also include a conventional working channel WC, as illustrated in broken line in FIG. 12A.

Figure 12B:
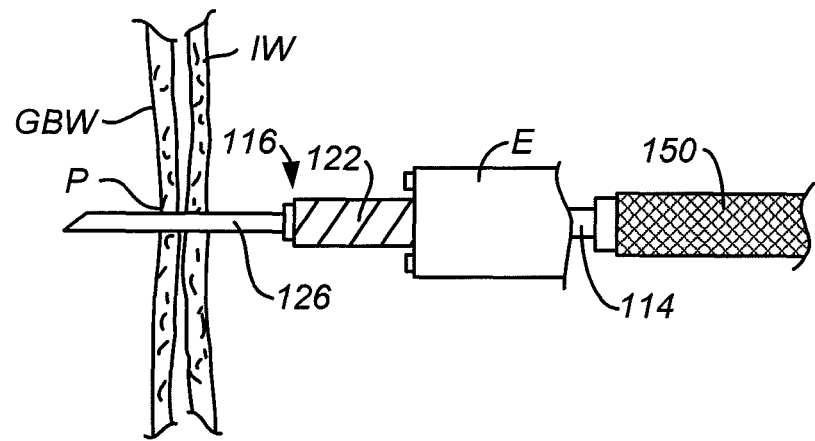

Referring now to FIG. 12B, the luminal wall connection system 100 will be introduced through the working channel WC so that the distal end 116 of the catheter 114 is brought adjacent to the walls GBW and IW. The needle 126 may then be advanced through the walls to form an initial penetration.

Figure 12C:
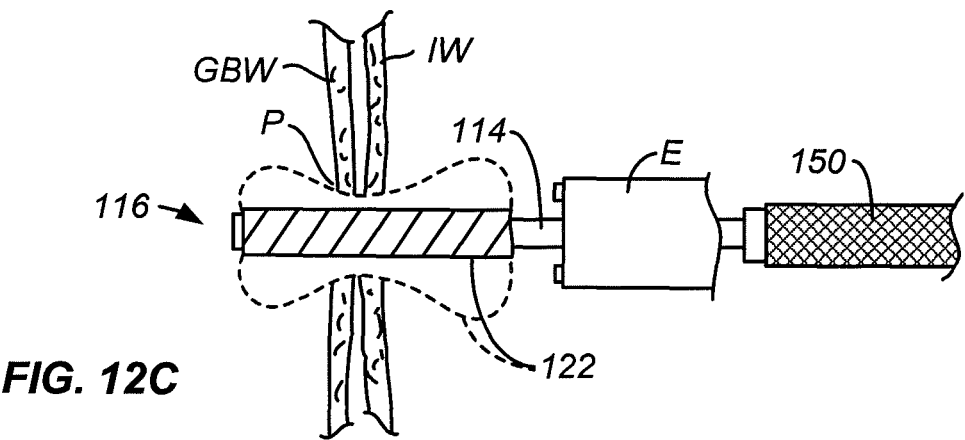

The uninflated balloon 122 will be advanced into the penetration, usually over the needle 126, as shown in FIG. 12C. The balloon may then be inflated, typically assuming a standard hot dog, top hat or dog bone pattern, said top hat having the distal end where the proximal and distal ends are wider (e.g., have a larger diameter) than the central and distal regions. Proximal movement of the top-hat balloon will pull the GBW and the IW walls together. The penetration P is thus expanded prior to placement of the stent 150.

Figure 12D:
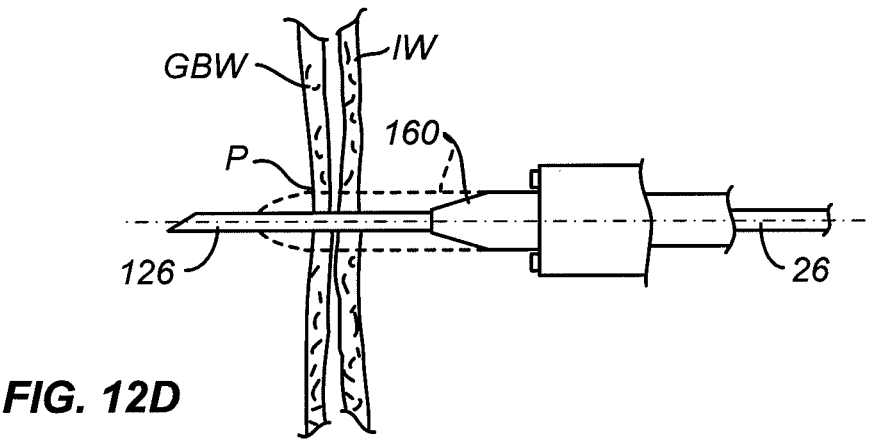

Referring to FIG. 12D, as an alternative to using balloon 122, the penetration P can be expanded using a tapered dilator 160 which may be advanced directly over the needle through the endoscope. Optionally, a tapered dilator may be formed as a distal extension of the outer tubular member 136 (not shown).

Figure 12E:
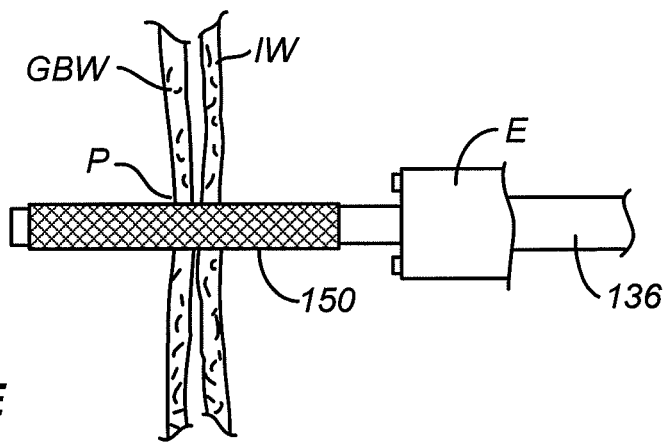
Figures 12F, 12G:
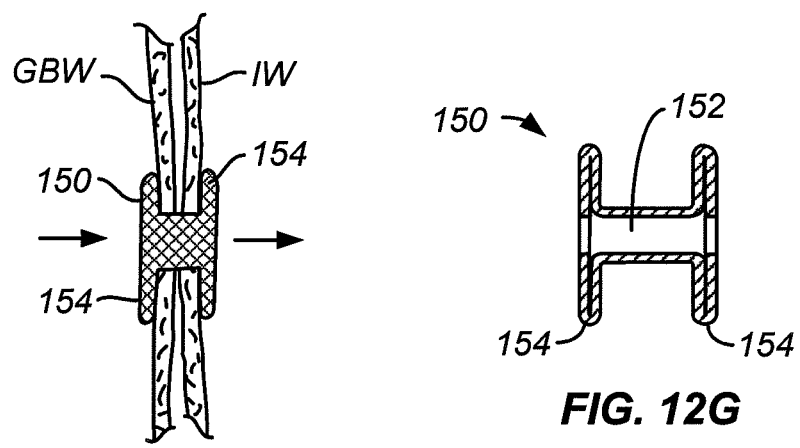

Referring now to FIG. 12E, after the penetration P has been expanded, the outer tubular member 136 will be advanced so that the stent 150 is located in the expanded penetration. A stent 150 is then expanded, as shown in FIG. 12F, typically by foreshortening, as will be described in more detail below. Preferably, the proximal and distal ends of the stent 150 will be expanded or flared to form relatively large flange regions 154 which act to tightly hold the gallbladder wall GBW and intestinal wall IW together to promote tissue knitting or ingrowth to inhibit leakage from either the gallbladder or the intestines. Once in place, the stent 150 forms a central lumen 152 (FIG. 12G) which provides a flow path as indicated by the arrows in FIG. 12F from the gallbladder to the intestines.

Following formation of a fistula or anastomosis the stent can optionally be removed, the flow now being through a tissue fistula orifice.

An alternate method is to follow the needle 126 with the simultaneous movement of the outer tubular member 136 with stent 150 and balloon 122. The stent is then released from constraint, with proximal and distal flanges now expanding and holding the lumens together, this followed by balloon expansion of the saddle region of the stent by balloon 122 which is inside the partially collapsed saddle region. This post-expansion method allows the anchor stent to hold the tissues together during tract dilation which is desirable. [Add figures and description?] FIG. 11 new version will have stent on balloon Balloon is under saddle only While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for approximating tissue and forming an anastomosis between a gallbladder and a duodenum or stomach, said method comprising:
    forming aligned penetrations in two adjacent tissue layers of two anatomical lumens, a first of the two anatomical lumens being formed by the gallbladder and a second of the two anatomical lumens being formed by either the duodenum or the stomach;
    advancing a tissue anchor through said aligned penetrations, said anchor comprising a body having an axis and a woven filament braid, wherein said body is radially constrained in an elongated tubular configuration while being advanced, and
    allowing the body to foreshorten into a preformed shape by self-expansion to cause a distal end and a proximal end of the body to each deform into a double-walled flange structure leaving a cylindrical saddle region therebetween, the saddle region having an open central lumen therethrough to provide a flow path through the adjacent tissue layers after the tissue anchor is in place, wherein the both walls of each flange structure lie perpendicular to the axis and the flange structures press against the tissue layers with the saddle region disposed in the penetrations, wherein the both walls of each flange structure and the cylindrical saddle region therebetween comprise a continuous woven filament braid having an elastomeric material formed over the braid such that the material conforms to the body in both the elongated and foreshortened configurations, the material being configured to prevent or inhibit tissue ingrowth, to minimize fluid leakage from the anatomical lumens and from the lumen of the saddle region, and to allow the anchor to be removed after having been implanted for weeks, months, or longer, the material being configured to allow fluid flow through each flange structure and the cylindrical saddle region between the anatomical lumens.

2. A method as in claim 1, wherein the body is foreshortened to apply sufficient pressure to the tissue layers to hold them together without causing significant tissue necrosis or adhesion.

3. A method as in claim 2, wherein the applied pressure is in the range from 0.025 psi to 2.5 psi.

4. A method as in claim 1, wherein forming and advancing comprise positioning a catheter near a target location on a tissue wall within one of said anatomical lumens, advancing a penetrating element from the catheter to form the penetrations, and advancing the catheter through the penetrations to position the tissue anchor therethrough prior to foreshortening.

5. A method as in claim 1, wherein foreshortening comprises releasing the elongated tubular body from constraint so that the flanges self-expand.

6. A method as in claim 1, wherein a valve, interposed within the body, provides a one way flow control allowing flow from the gallbladder and into the duodenum or stomach without reflux.

* * * * *